United States Patent

Gazzani

Patent Number: 5,182,269
Date of Patent: Jan. 26, 1993

[54] COMPOSITION FOR TOPICAL USE HAVING HAIR STIMULATING, ANTI-DANDRUFF AND ANTI-SEBORRHOIC ACTIVITY

[75] Inventor: Giovanni Gazzani, Appiano Gentile, Italy

[73] Assignee: Crinos Industria Farmacobiologica SpA, Como, Italy

[21] Appl. No.: 652,499

[22] Filed: Feb. 11, 1991

Related U.S. Application Data

[62] Division of Ser. No. 248,692, Sep. 23, 1988, abandoned.

Foreign Application Priority Data

Sep. 23, 1987 [IT] Italy ................. 21990 A/87

[51] Int. Cl.$^5$ .................. A61K 31/70; A61K 7/06; A61K 7/075
[52] U.S. Cl. .................. 514/44; 514/47; 514/880; 514/881; 514/852; 424/70
[58] Field of Search .................. 514/47, 44, 880, 881, 514/852; 424/70

[56] References Cited

U.S. PATENT DOCUMENTS

| | | | |
|---|---|---|---|
| 3,829,567 | 8/1974 | Butti et al. | 536/24 |
| 3,830,798 | 8/1974 | Herndon et al. | 536/24 |
| 3,838,148 | 9/1974 | Christen | 536/24 |
| 3,899,481 | 8/1975 | Butti et al. | 260/211.5 |
| 4,985,552 | 1/1991 | Fedeli et al. | 536/28 |

*Primary Examiner*—Ronald W. Griffin
*Attorney, Agent, or Firm*—Nikaido, Marmelstein, Murray & Oram

[57] ABSTRACT

Depolymerized deoxyribonucleic acid containing weight amounts of purine and pyrimidine bases such that the related molar ratio purinea/pyrimidines is comprised within a determined range and having moreover molecular weights limited to a determined range of values of less than 100,000 are endowed with remarkable hair stimulating activity.

11 Claims, 2 Drawing Sheets

COMPOSITION FOR TOPICAL USE HAVING HAIR STIMULATING, ANTI-DANDRUFF AND ANTI-SEBORRHOIC ACTIVITY

This application is a division of application Ser. No. 248,692 filed Sep. 23, 1988, now abandoned.

The present invention relates to the description of the chemical and chemico-physical characteristics of depolymerized nucleic acids having high hair stimulating activity and to the cosmetic preparations containing them.

It can be stated that the use of the these substances in the cosmetic field is known since long time.

As a matter of fact it is known (P. Rovesti "Nucleic acids in cosmetology" parfum. oosm. Savons I 398–402 1958) that the nucleic acids have toning up, restituting and emollient activity towards the skin. Their use by the way has been foreseen also in cosmetic compositions for the hair wave set (U.S. Pat. No. 2,960,442), with relation to the fact that said substances, owing to their high molecular weight and to the characteristic alongated shape of the polymer, are able to form thin films with a determined orientation.

The FR-A-1361925 discloses the use of depolymerized nucleic acids, with molecular weight lower than 100,000, in combination with a greater amount of aminoacids and peptides which are contained in the hydrolisates of cutaneous tissues of animals obtained in acidic and alkaline conditions, a mixture of the extracts being provided at the very end.

It is worth to note that in the cosmetic compositions foreseen in this reference the amount of the above mixture of hydrolisates is on the whole 10% whereas that of the solutions containing the depolymerized nucleic acids is only 0.2%.

In this connection it is to be pointed out that, it being not possible to prepare solutions of these polymers at a concentration greater than 10% w/v, it can be reasonable supposed that the amount of nucleic acids contained in the above cosmetic compositions in any way was not greater than 0.02%, which would represent an amount 50 times lower than the minimum one foreseen in the compositions according to the present invention. It is doubtful under these conditions that any activity whatsoever on hair regrowth due to use of these substances can be appreciated. The Applicant, on the basis of the tests carried out in its laboratories has observed that at concentrations lower than 0.1% (w/v.) the nucleic acids are not active on the hair stimulation, even with extended treatments.

Besides these considerations, the Applicant has assessed, as it will be extensively reported hereinafter, that the nucleic acids, with molecular weight lower than the limit of 100,000 indicated by the above French Patent, have an activity very different depending on the fact that the polymer belongs to the class of the deoxyribonucleic or ribonucleic acids, it having been found that only the former are active.

Furthermore, as relates particularly to the deoxyribonucleic acids, it has been also demonstrated that the hair stimulating activity depends, apart from the reduced molecular weight, in a critical manner from the presence in these macromolecules of determined amounts of some constituents, particularly purine bases.

It has been lastly observed that, below the molecular weight of 100,000, there exists an interval of molecular weights in which the hair stimulating activity of the depolymerized deoxyribonucleic acids is higher.

In order to complete the picture of the prior art, it is worth to mention also the French Patent 1,603,826 which discloses the use of cosmetic compositions containing as the active ingredients a mixture of deoxyribonucleic and ribonucleic acids in total amounts of between 0.1 and 0.5%. Said formulations are useful as creams, soaps, etc. The function of the nucleic acids in said formulations is particularly that of promoting the changeover, in the cutaneous tissues, of old or death cells with young cells.

It is evident that from the above patent no teaching can be obtained with respect to the hair stimulating activity of the depolymerized deoxyribonucleic acids and with respect to the dependency thereof, for example from the presence in the macromolecule of determined amounts of some components.

The interest for the use of the nucleic acids, particularly deoxyribonucleic acids, in the cosmetic field, can be at the very end attributed to two factors, and precisely to the fact that these substances are present in several animal organs, besides the human being obviously, in which they fulfill important biological functions. Secondly they are raw materials which are readily available as by products of the extracting industry. In the laboratories of the applicant the investigation on the hair stimulating activity of the nucleic acids has been initially directed to the evaluation of deoxyribonucleic and ribonucleic acids. The former have been obtained from the market or directly from the suppliers of the raw materials.

The preparations of ribonucleic acid have been on the contrary obtained directly in the laboratories of the Applicant by using the standard methods, the extraction from the organ being carried under alkaline conditions.

The method used to evaluate the hair stimulating activity consists in the observation of the hair regrowth on the shaved back of rabbits, at determined times, after having injected in several areas, as hereinafterr specified, the solution of the nucleic acids.

For each sample a group of animals consisting of two rabbits was provided.

The injections were carried out on the back at two different levels and for each level in two areas symmetrical with respect to the backbone. The amount of injected solution was of 0.1 ml of physiological solution in which the substances had been dissolved at a concentration of 1% w/v. At a level different from the previous ones, but under the same conditions, also the physiological solution as such was injected, in order to have an internal standard on the basis of which the importance of the hair regrowth which was observed could be evaluated.

A score was then attributed on the basis of the following scale:
- − no regrowth
- +− just evident regrowth
- + evident regrowth
- ++ good regrowth
- +++ abundant regrowth.

The injections were repeated for five consegutive days. After fifteen days from that of the first injection and then after thirty and sixthy days the hair regrowth was observed and the score was attributed according to the above criteria.

It is worth to note that this method permits a much quicker evaluation of the hair stimulating activity of the tested samples and leads to a relevant time saving with respect to the method in which the lotion is on the contrary topically applied to the animal cutis.

Moreover, the amounts required to carried out the experiment are definitely lower.

The nucleic acids were moreover characterized by the following parameters:

Molecular weight, determined by light scattering. The substance was initially dissolved, at a determined concentration, in a saline solution 0.01M NaCl and 0.0013M of phosphate buffer. The method for the preparation of the solution and for the subsequent dilution, as well as the process for the determination of the molecular weight, is described by G. Bernardi, Makrom. Chem. 72 205 1964.

BRIEF DESCRIPTION OF THE DRAWINGS:

Examples of determination of the molecular weights of the nucleic acids by this technique are reported in the graphs of FIGS. 1, 2, 1B, 2A and 2B. In those graphs in the abscissae the concentration (g/l or g/ml) is indicated, whereas in the ordinates the ratio $C/I_{90}$ indicating the concentration (C) in g/ml divided by $I_{90}$, representing the intensity of the scattered light measured at 90° with respect to the incident light beam.

The molecular weights are than calculated by the formula:

Figure 1A:
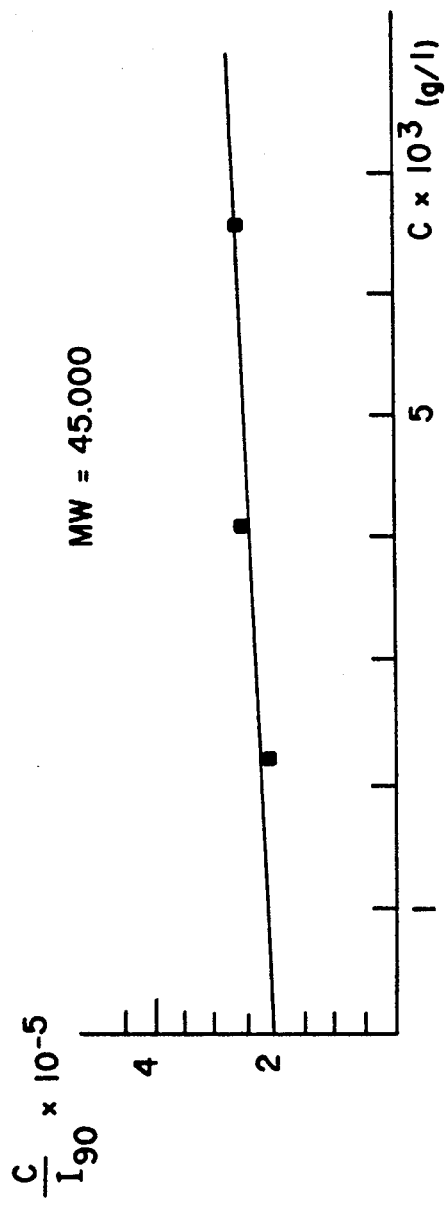
Figure 1B:
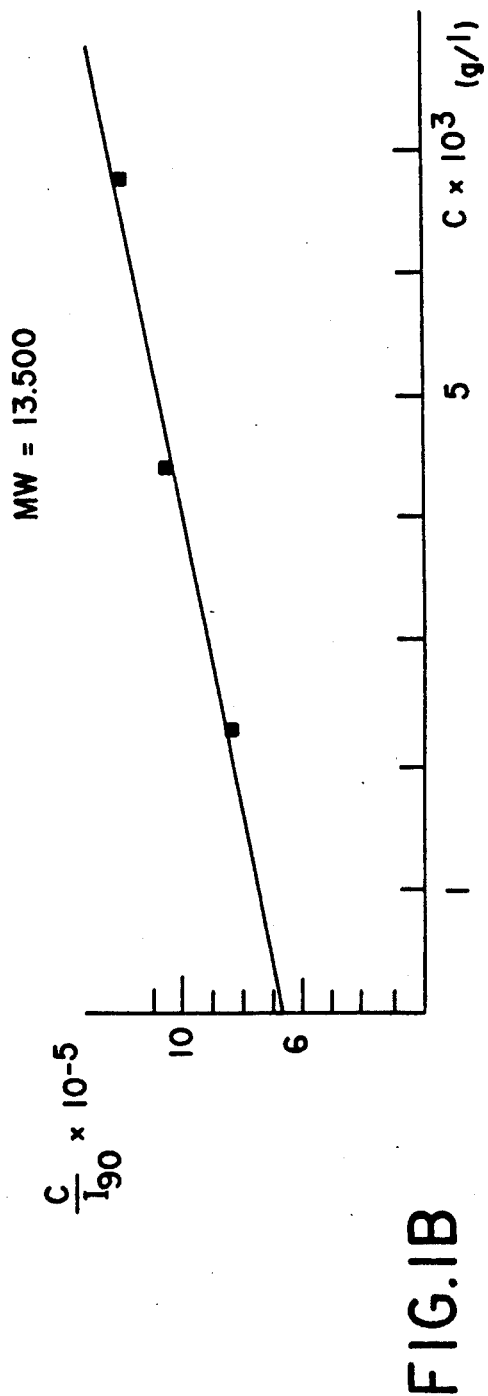
Figure 2A:
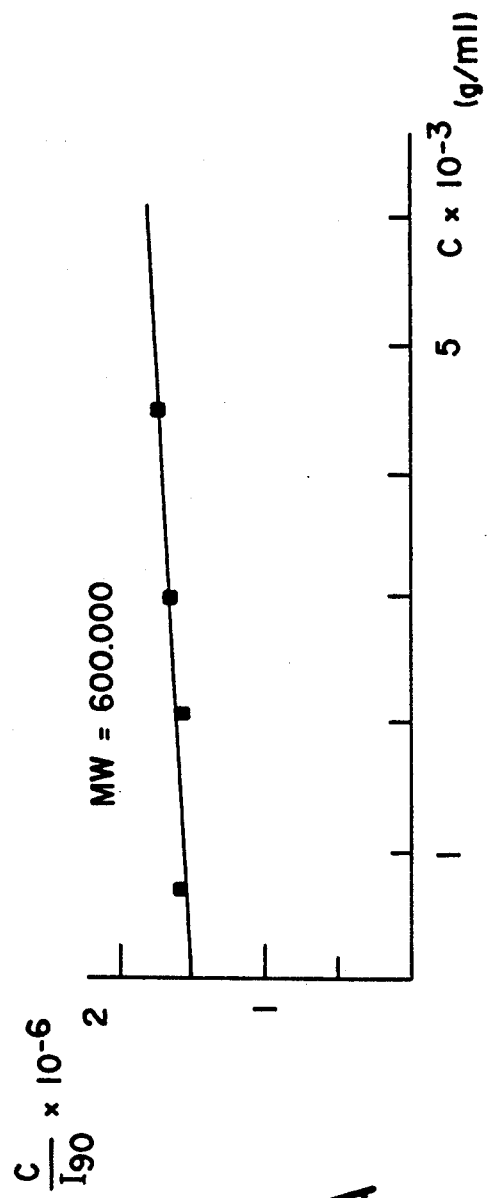
Figure 2B:
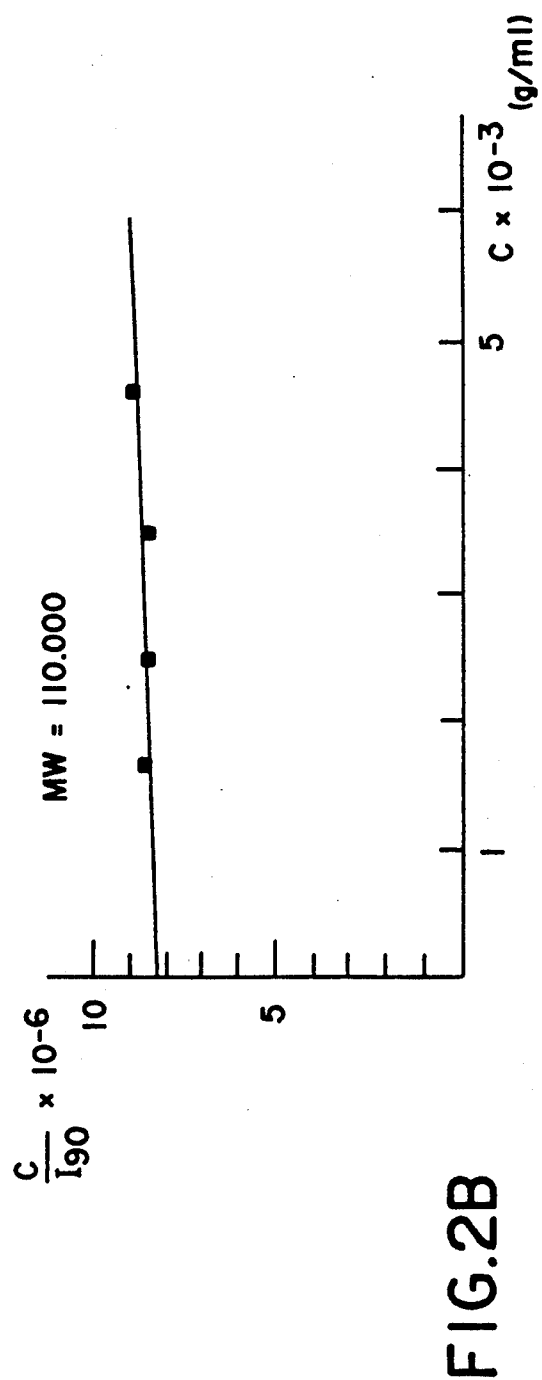

$$1/M_w - 0.0183 \times I_B \times (C/I_{90})_c = 0$$

in which IB is a constant, which in this case has a numerical value of 60 and the last term represents the value of the ordinates at the interception with the regression straight line.

In the case that samples with known molecular weight were available with the above methods, the determination was carried out, after a suitable calibration, by HPLC on a Zorbax column packed with silica gel, the matrix of which had bonded substituents having vicinal diol groups. The eluant is 0.05M phosphate buffer (pH5) and 0.1M KCl.

Phosphorus, determined according to the method of Fiske and Subarrow, J. Biol. Chem. 66, 375 1925.

Deoxyribose, according to the method described in Methods in Enzymol. vol. III, page 680.

Purinic and pyrimidinic bases, determined after hydrolysis of the sample (20 mg) carried out by means of 0.4 ml of concentrated perchloric acid at 100° C. for 45 minutes in a sealed ampule saturated with nitrogen, by high pressure liquid cromatography on a ion exchange resin.

In Table 1 data relating to the molecular weight of these preparations and to the corresponding hair stimulating activity are reported. Table 2 relates instead to the chemical data.

TABLE 1

Molecular weight and corresponding hair regrowth of some samples of deoxyribonucleic and ribonucleic acids available from the market, or from suppliers or directly isolated in the laboratories of the applicant.

| Substance | m.w. × 10³ | hair regrowth 15 days | 30 days | 60 days |
| --- | --- | --- | --- | --- |
| DNA from calf thyme | 1,200 | — | — | — |
| DNA from salmon sperm | 850 | — | — | — |
| DNA from bovine pancreas | 630 | — | — | — |
| DNA from bovine lung | 220 | — | — | — |
| RNA from yeast | 110 | — | — | — |
| RNA from calf pancreas I | 71 | — | — | — |
| RNA from calf pancreas II | 38 | — | — | — |
| RNA from rat liver | 24 | — | — | — |

TABLE 2

Chemical parameters of the nucleic acids reported in preceeding Table 1.

| Substance | Phosphorus | Adenine % | Guanine % | Cytosine % | Uracil % | Thymine % | $\frac{A+G}{T+C}$ |
| --- | --- | --- | --- | --- | --- | --- | --- |
| DNA from calf tyme | 8.5 | 9.98 | 8.88 | 6.09 | — | 9.73 | 0.98 |
| DNA from salmon sperma | 8.33 | 10.55 | 8.26 | 5.86 | — | 9.65 | 1.05 |
| DNA from bovine pancreas | 8.41 | 9.80 | 8.64 | 6.29 | — | 9.38 | 0.99 |
| DNA from bovine lung | 8.12 | 9.40 | 9.20 | 6.30 | — | 8.10 | 1.08 |
| RNA from yeast | 8.25 | 8.92 | 9.66 | 6.54 | 7.98 | — | |
| RNA from calf pancreas I | 8.50 | 10.57 | 10.86 | 11.20 | 9.92 | — | |
| RNA from rat liver | 8.40 | 7.15 | 10.18 | 8.59 | 7.22 | — | |

The data are referred to dry basis.

$\frac{A+G}{C+T}$ means the ratio between the sum of the purinic (A + G) and pyrimidinic bases (C + T).

From the data reported in Table 1 it is seen that the deoxyribonucleic acids with high molecular weight have no activity towards the regrowth in the hair in the animals, as well as the preparations of ribonucleic acids with reduced molecular weight which are considered in the same table. As a consequence of the results obtained in these experiments, taking also it into account the absence of efficacy of the ribonucleic acids, even if with reduced molecular weight, the Applicant has prepared in its own laboratories deoxyribonucleic acids with low molecular weight, obtained by depolymerization in acidic environment, using methods known in the literature. (C. Tamm et Alii "Physical and chemical properties of apurinic acid of calf thymus" J. Biol. Chem. 203 689 1953; C. Tamm et Alii "The formation of apurinic acid from deoxyribonucleic acid of calf thymus" J. Bio. Chem. 195 49 1952; W. Cohn "acid degradation products of deoxyribonucleic acid" Biochim. Biophys. Acta 24 359 1957). In this connection it is to be observed that it is possible to carry out the depolymerization of deoxyribonucleic acid also in alkaline environment, which however has the drawback of causing also a partial degradation of some components of the macromolecule (R. O. Hurst et Alii "degradation of deoxyribonucleic acid by hot alkali", Can J. Biochem. and Physiol. 36 919 1958; N. K. Kotchekov et Alii" organic chemistry of nucleic acids" page 385 and 504 Plenum Press London 1972). The presence in the product of these substances which, as already stated, are originated by the alkaline conditions used for the depolymerization makes it obviously necessary a preliminary determination of the possible toxicity with respect to the subsequent use in formulations to be used by topical route.

For these reasons the preparations of depolymerized deoxyribonucleic acids have been obtained with the above mentioned method.

Starting thus from nucleic acids obtained from lung and using different acidity conditions, (see examples 1–5 in this connection), the preparations having the analytical characteristics reported in Table 3 have been obtained.

In Table 4 for the same preparations the results of the hair stimulating activity tests are reported together with the most important analytical parameters in order to define the scope of the present invention.

It can be thus observed that below of molecular weight of 100,000 which by the way is already indicated by the prior art (French Patent FR-A-1361925) there are some preparations which are not active together with others which on the contrary possess a moreorless evident activity. It is worth to note moreover that the above activity can be related, on the basis on the results which have obtained in these experiments, with the ratio between the purinic and pyrimidinic bases and, at a very end, with the fact that in the macromolecule determined amounts of these bases are present.

From the table it is thus observed that the activity of these preparations becomes lower as the aforesaid ratio is reduced.

It can be observed that the preparation DNA D 4, having a molecular weight of 18,000 and a ratio between purine and pyrimidine bases of 0.15, is not active. The preparations DNA D2 and DNA D5 with molecular weights and bases ratio respectively of 28,000 and 41,000, 0.61 and 0.74 give place instead to a just evident hair regrowth. Highly active are on the contrary the preparations DNA D1 and DNA D3 (molecular weight of 83,000 and 53,000 respectively bases ratio of 0.91). In that case it is moreover observed that the preparation with lower molecular weight (53,000) is more active than the other.

Resuming thus the results obtained to date with respect with to what was already known in this field before the filing of the present application, it was not foreseable that the ribonucleic acids with molecular weight lower than 100,000 would be devoid of activity in the particular cosmetic use to which in the present invention is aimed at.

Moreover it was not foreseable as well that depolymerized deoxyribonucleic acids with molecular weight lower than the above indicated values would have an activity which can be related to the ratio between the purine and pyrimidine bases and thus at a very end, as already stated, to the presence in the macromolecule of determined amounts of these compounds.

The data reported in the above table together with those of the next table 5 and with the subsequent examples 6 and 7, permit above all the following variation limits to be defined for the chemical parameters of these substances, active in the hair stimulation and having a reduced molecular weight, the variation range of which shall be defined hereinafter:

| | |
|---|---|
| Phosphorus: | 8–9.6% |
| Nitrogen: | 13–15% |
| Deoxyribose: | 17–24% |
| Adenine: | 8.0–10.0% |
| Guanine: | 7.0–9.5% |
| Cytosine: | 5.5–7.5% |
| Thymine: | 8.0–11.0% |
| $\frac{A+G}{T+C}$ | 0.87–1.01% |

The data are given on dry basis.

Another feature of the present invention resides in that a range of molecular weights has been individuated in which said depolymerized deoxyribonucleic acids show an improved hair stimulating activity and a narrower range in which the above activity takes its highest value.

Coming back to table 4, it is worth to note that the preparations DNA D1 and DNA D3, although having the same values as regards the ratio between purine and pyrimidine bases, show a different activity which can be clearly related to the corresponding molecular weight of the two substances.

On the basis of these results a further series of experiments has been carried out by preparing the depolymerized nucleic acids having different molecular weight within the range from 10,000 to 100,000.

Moreover with respect to the fact said acids must have a ratio between the moles of purine bases and those of the corresponding pyrimidine bases within a determined range, the prior art has been investigated to as-

TABLE 3

Analytical characterization of the starting nucleic acids and of the corresponding preparations obtained by depolymerization under different acidity conditions. In brackets the example is indicated in which the corresponding process is described.

| Substance | m.w. × 10⁻³ | Phosphorus % | Adenine % | Guanine % | Cytosine % | Thymine % | $\frac{A+G}{T+C}$ |
|---|---|---|---|---|---|---|---|
| DNA from bovine lung | 600 | 8.35 | 9.75 | 9.04 | 6.43 | 8.59 | 1.05 |
| DNA D1 (ex. 1) | 83 | 8.50 | 9.40 | 7.50 | 6.60 | 8.90 | 0.91 |
| DNA D2 (ex. 2) | 28 | 8.98 | 6.14 | 5.80 | 6.90 | 9.30 | 0.61 |
| DNA from bovine lung | 320 | 7.90 | 9.50 | 9.30 | 6.50 | 8.91 | 1.00 |
| DNA D3 (ex. 3) | 53 | 8.24 | 9.15 | 7.98 | 6.69 | 9.26 | 0.91 |
| DNA D4 (ex. 4) | 18 | 9.55 | 1.14 | 2.58 | 8.1 | 11.80 | 0.15 |
| DNA from salmon sperma (table 2) | 850 | 8.33 | 10.55 | 8.26 | 5.86 | 9.73 | 1.05 |
| DNA D5 (ex. 5) | 41 | 9.21 | 7.17 | 6.11 | 5.84 | 9.20 | 0.74 |

Evaluation of the activity on the hair regrowth in the rabbit of the preparations of depolymerized deoxyribonucleic acids of the previous table.

| | | | Hair regrowth in the rabbit observation times (days) | |
|---|---|---|---|---|
| Substance | m.w. × 10⁻³ | $\frac{A+G}{C+T}$ | 15 days | 30 days | 60 days |
| DNA D1 | 83 | 0.91 | + | + | ++ |
| DNA D2 | 28 | 0.61 | − | − | +− |
| DNA D3 | 53 | 0.91 | + | ++ | +++ |
| DNA D4 | 18 | 0.15 | − | − | − |
| DNA D5 | 41 | 0.74 | − | −+ | −+ | sess whether polymerization processes were available which would be at the same time faster than those used to date and that moreover would permit, by suitably varying the experimental conditions (for example the depolymerization time), to easily obtain preparations with a molecular weight even relevantly different from each other although within the above limits.

It has been found that the depolymerization process disclosed in the U.S. Pat. No. 3,899,481 was suitable to achieve the above purpose and it has been thus used for the preparation of the deoxyribonucleic acids with reduced molecular weight which have been used in the experiments to be explained hereinafter.

The starting deoxyribonucleic acids had been obtained from small gut, (examples 6 and 7) or from lung. In the latter case the polymers were treated under the condition, described in the above mentioned example 6 and consequently their preparation is not detailedly reported.

The table 5 reports the characteristics of these products.

In the same table, as it can be observed, a preparation (DNA D11) has been also included, which was obtained by carrying out a further depolymerization process on a preparation already obtained from a like treatment (DNA D6).

From the table 6, illustrating the hair stimulating activity of these different substances, it can be firstly observed that a very relevant activity on the hair regrowth is shown by the deoxyribonucleic acids having a molecular weight of between 80,000 (preparation DNA D1 of table 4) and 20,000, having a chemical composition within the limits previously indicated.

Within this interval another one is individuated, of between 60,000 and 20,000, in which the said activity is still higher. It is to be noted that the preparations having molecular weight lower than 20,000 (as in the case of the preparation DNA D11) are less active on the hair stimulation.

Thus, as a conclusion, although in the prior art there was already indicated that the nucleic acids in order to be active in the hair stimulation had to be of reduced molecular weight, it was not absolutely foreseeable neither that the depolymerized ribonucleic acids would not be active nor that the depolymerized deoxyribonucleic acids would be active only in a determined field of composition of purine and pyrimidine bases defined, apart from the related weight percentages, also from the corresponding ratio between the total moles of purine bases and those of the corresponding pyrimidine bases.

TABLE 6

Evaluation of the activity on the hair regrowth in the rabbit of the preparations of deoxyribonucleic acids of Table 5.

| Substance | m.w. $\times 10^{-3}$ | $\frac{A+G}{C+T}$ | Hair regrowth in the rabbit observation times (days) | | |
|---|---|---|---|---|---|
| | | | 15 days | 30 days | 60 days |
| DNA D6 | 30 | 0.94 | ++ | ++ | +++ |
| DNA D7 | 110 | 0.95 | − | −+ | + |
| DNA D8 | 22 | 0.99 | ++ | ++ | +++ |
| DNA D9 | 57 | 1.00 | ++ | ++ | +++ |
| DNA D10 | 73 | 1.00 | + | ++ | ++ |
| DNA D11 | 11 | 0.90 | − | + | + |

Lastly, it was in no way foreseable that the depolymerized deoxyribonucleic acids, falling within the limits of molecular weight of the above mentioned FR-A-1361925 and having moreover a chemical composition according to the above analytical indication, had a different hair stimulating activity with respect to determined values of their molecular weight, (as defined within the previously determined limits).

It is to be lastly observed that the organs from which the deoxyribonucleic acids have been initially extracted and which are mentioned in the previous tables as well as in the next examples 1–7 must not be meant in any manner as limiting the scope of the present invention, since it is well known to the skilled persons, that depolymerized deoxyribonucleic acid having the herein described characteristics can be obtained also from nucleic acids originating from other sources, such as pancreas, placenta, bovine thyme, spleen, liver, kidney, etc.

The efficacy of the depolymerized deoxyribonucleic acids has been assessed also as regards the stimulation of the hair growth in the human being.

To this end a test has been carried out on 20 volunteers suffering from androgenetic alopecia.

The deoxyribonucleic acids (molecular weight 30,000) were prepared in a formulation having the composition shown in the subsequent example 9 (final concentration 2.5%).

The scalp of patients was daily frictioned with 7 ml of the cosmetic formulation. The treatment was regularly repeated for 60 days on the whole.

The volunteers were free of carrying out in any moment a hair washing provided that immediately after the above treatment was carried out. The controls of the hair conditions, of the dandruff and the of seborrhea, were carried out after 30, 60 and 90 days from the starting of the experiments and the evaluation was based on subjective parameters. The obtained results have shown a significant improvement both as regards the hair con-

TABLE 5

Analytical characteristics of the depolymerized deoxyribonucleic acids obtained with the process of U.S. Pat. No. 3,899,481

| Substance | m.w. $\times 10^{-3}$ | P* | D.O. Ribose** | A*** | G*** | C*** | T*** | $\frac{A+G}{T+C}$ |
|---|---|---|---|---|---|---|---|---|
| DNA D6 (ex. 6) | 30 | 8.63 | 23.5 | 9.30 | 7.85 | 6.36 | 9.14 | 0.94 |
| DNA D7 (ex. 7) | 106 | 8.40 | 20.4 | 9.60 | 8.10 | 6.72 | 8.83 | 0.95 |
| DNA D8**** | 22 | 8.45 | 18.1 | 8.68 | 8.88 | 6.33 | 8.43 | 0.99 |
| DNA D9**** | 57 | 8.86 | 19.6 | 9.35 | 8.52 | 5.70 | 9.23 | 1.00 |
| DNA D10**** | 73 | 8.57 | 19.0 | 9.31 | 8.35 | 5.70 | 9.05 | 1.00 |
| DNA D11 | 11 | 9.20 | 24.0 | 9.00 | 7.41 | 5.81 | 9.70 | 0.90 |

*Phosphorus;
**Deoxyribose;
***respectively in the order: Adenine, Guanine, cytosine, thymine
****preparations obtained by depolymerization under the conditions of example 6, of DNA from lung.

dition and as regards the stopping of their fall, which occurred in a progressive manner.

It is has been also observed that the hair regrowth was greater in these cases in which alopecia occurred from a lesser time. Very probably said phenomon can be attributed to the fact that in these cases the hair follicles were not yet in an advanced atrophic status.

It has been moreover assessed that the dandruff secretion and seborrhea were reduced to physiological limits.

The cosmetic compositions foreseen according for the present invention are in the form of a lotion having a concentration of depolymerized deoxyribonucleic acid of between 1 and 5%.

The examples 9 and 10 report, as non limiting examples, said formulations.

EXAMPLE 1

50 g of nucleic acid from lung (analytical characteristics given in table 3) are dissolved in 3.5 liters of distilled water, HCl is added until the pH is lowered to 2.7. The solution is maintained at 37° C. for 24 hours. It is neutralized with NaOH. It is dialized for 24 hours and then salted with NaCl up to a concentration of 1% and 1.8 volumes of acetone are added.

There are recovered 42 g. The analytical parameters of the obtained product are reported in table 3 (preparation DNA D1).

EXAMPLE 2

50 g of nucleic acid from bovine lung (analytical characteristics given in table 3) are dissolved in distilled water at a concentration indicated in the above example 1.

Concentrated HCl is added up to pH 2.1. Then the hydrolysis is carried out under the same conditions as before and likewise for the next recovery of the product.

There are obtained 37 g (preparation DNA D2).

EXAMPLE 3

50 g of nucleic acid from bovine lung (molecular weight 320,000 analytical characteristics given in table 3, are treated likewise the example 1. There are recovered 45 g (preparation DNA D3).

EXAMPLE 4

50 g of nucleic acid from bovine lung of the previous example 3 are dissolved as described in the preceeding example 1. The pH is adjusted to the value of 0.1 and then the process described in the same example is followed.

There are obtained 30 g of product (preparation DNA D4).

EXAMPLE 5

10 g of the deoxyribonucleic acid from salmon sperm, the analytical characteristics of which are reported in table 3, are dissolved in 500 ml of distilled water. Upon the dissolution is completed, concentrated HCl is added up to pH 2.3. By proceeding as described in example 1 there are obtained 6 g of depolymerized deoxyribonucleic acid, (preparation DNA D5).

EXAMPLE 6

50 g of deoxyribonucleic acid from small gut having the following analytical parameters: phosphorus 8.1%, deoxyribose 23.1%; adenine 9.87%; guanine 8.53%; cytosine 6.96%; thymine 8.56%; are dissolved in one liter of 0.47M sodium acetate buffer M at a temperature of 55° C.

Upon the dissolution is completed, 150 g of 80% acetic acid are added so as to adjust the pH of the solution to 4.

The solution is then heated at 70° C. for 4 hours. At the end it is cooled, the pH is adjusted to 8 and the product is precipitated by adding two volumes of ethyl alcohol.

There are obtained 35 g of deoxyribonucleic acid having the analytical characteristics reported in table 5 (preparation DNA D6).

EXAMPLE 7

50 g of the deoxyribonucleic acid from small gut of the preceeding example are depolymerized as described for a time of 1.5 hours. The product which is isolated (40 g) has the characteristics shown in the table 5 (preparation DNA D7).

EXAMPLE 8

20 g of the preparation DNA D6 are subjected to the same depolymerization process which in the example 6 is reported for the deoxyribonucleic acid from small gut.

12 g of product are obtained (preparation DNA D11) the analytical parameters of which are reported in table 5.

EXAMPLE 9

|  | A | B | C |
|---|---|---|---|
| Hair lotion (normal type) | | | |
| Depolymerized deoxyribonucleic acids g | 1 | 1.5 | 2.5 |
| ethyl alcohol ml | 15 | 15 | 15 |
| perfume | enough | enough | enough |
| preservants | enough | enough | enough |
| water enough to ml | 100 | 100 | 100 |
| Example 10 | | | |
| Hair lotion (strong type) | | | |
| Depolymerized deoxyribonucleic acids g | 4 | 5 | |
| ethyl alcohol ml | 15 | 15 | |
| perfume | enough | enough | |
| preservants | enough | enough | |
| water enough to ml | 100 | 100 | |

I claim:

1. A method for stimulating the growth of hair which comprises applying to the scalp of a patient a hair-growth stimulating amount of a depolymerized deoxyribonucleic acid having the following analytical composition:

| molecular weight | 180,000–20,000 Daltons |
|---|---|
| total nitrogen | 13–15% |
| total phosphorus | 8–9.6 % |
| deoxyribose | 17–24% |
| adenine | 8–10% |
| guanine | 7–9.5% |
| cytosine | 5.5–7.5% |
| thymine | 8–11% |
| $\dfrac{A + G}{T + C}$ | 0.87–1.01% | the percentage data being on dry basis.

2. A method according to claim 1, wherein the depolymerized deoxyribonucleic acid has a molecular weight of between 60,000 and 20,000 Daltons.

3. A method according to claim 1, wherein the depolymerized deoxyribonucleic acid has a molecular weight of 30,000 Daltons.

4. A method according to claim 1, wherein the depolymerized deoxyribonucleic acid has the following analytical composition:

| | |
|---|---|
| molecular weight | 53,000 Daltons |
| phosphorus | 8.24% |
| adenine | 9.15% |
| guanine | 7.98% |
| cytosine | 6.69% |
| thymine | 9.26% |
| $\frac{A + G}{T + C}$ | 0.91%. |

5. A method according to claim 1, wherein the depolymerized deoxynucleic acid has the following analytical composition:

| | |
|---|---|
| molecular weight | 30,000 Daltons |
| phosphorus | 8.63% |
| adenine | 9.30% |
| guanine | 7.85% |
| cytosine | 6.36% |
| thymine | 9.14% |
| $\frac{A + G}{T + C}$ | 0.94%. |

6. A method according to claim 1, wherein the depolymerized deoxynucleic acid has the following analytical composition:

| | |
|---|---|
| molecular weight | 22,000 Daltons |
| phosphorus | 8.45% |
| adenine | 8.68% |
| guanine | 8.88% |
| cytosine | 6.33% |
| thymine | 8.43% |
| $\frac{A + G}{T + C}$ | 0.99%. |

7. A method according to claim 1, wherein depolymerized deoxynucleic acid has the following analytical composition:

| | |
|---|---|
| molecular weight | 57,000 Daltons |
| phosphorus | 8.86% |
| adenine | 9.35% |
| guanine | 8.52% |
| cytosine | 5.70% |
| thymine | 9.23% |
| $\frac{A + G}{T + C}$ | 1.00%. |

8. A method according to claim 1, wherein the depolymerized deoxynucleic acid has the following analytical composition:

| | |
|---|---|
| molecular weight | 73,000 Daltons |
| phosphorus | 8.57% |
| adenine | 9.31% |
| guanine | 8.35% |
| cytosine | 5.70% |
| thymine | 9.05% |
| $\frac{A + G}{T + C}$ | 1.00%. |

9. The method as claimed in claim 1 wherein said need thereof is baldness as the result of androgenetic alopecia.

10. The method as claimed in claim 1 wherein said composition has a ratio of purines to pyrimidines of 0.74 to 0.15.

11. The method as claimed in claim 1 wherein said composition consists essentially of depolymerized deoxyribonucleic acid.

* * * * *